United States Patent
Jureller et al.

(10) Patent No.: US 7,990,524 B2
(45) Date of Patent: Aug. 2, 2011

(54) STOCHASTIC SCANNING APPARATUS USING MULTIPHOTON MULTIFOCAL SOURCE

(75) Inventors: Justin E. Jureller, Chicago, IL (US); Hee Y. Kim, Chicago, IL (US); Norbert F. Scherer, Winnetka, IL (US)

(73) Assignee: The University of Chicago, Chicago, IL (US)

( * ) Notice: Subject to any disclaimer, the term of this patent is extended or adjusted under 35 U.S.C. 154(b) by 771 days.

(21) Appl. No.: 11/771,064

(22) Filed: Jun. 29, 2007

(65) Prior Publication Data

US 2008/0192231 A1 Aug. 14, 2008

Related U.S. Application Data

(60) Provisional application No. 60/818,195, filed on Jun. 30, 2006.

(51) Int. Cl.
*G01N 1/00* (2006.01)
(52) U.S. Cl. .......................................... 356/36
(58) Field of Classification Search .............. 356/36, 356/417
See application file for complete search history.

(56) References Cited

U.S. PATENT DOCUMENTS

| | | | |
|---|---|---|---|
| 5,677,093 A * | 10/1997 | Delabastita et al. | 430/30 |
| 5,734,498 A * | 3/1998 | Krasieva et al. | 359/387 |
| 5,858,589 A * | 1/1999 | Govaert et al. | 430/30 |
| 6,028,306 A * | 2/2000 | Hayashi | 250/235 |
| 6,128,077 A | 10/2000 | Jovin et al. | |
| 6,208,411 B1 | 3/2001 | Vaez-Iravani | |
| 6,278,521 B1 * | 8/2001 | Jablonski et al. | 356/402 |
| 6,399,935 B1 | 6/2002 | Jovin et al. | |
| 6,766,184 B2 * | 7/2004 | Utzinger et al. | 600/407 |
| 6,864,989 B2 * | 3/2005 | Storz et al. | 356/601 |
| 7,339,148 B2 * | 3/2008 | Kawano et al. | 250/201.3 |
| 7,492,535 B2 * | 2/2009 | Descour et al. | 359/818 |
| 7,698,000 B2 * | 4/2010 | Silberberg et al. | 700/1 |
| 2002/0043618 A1 * | 4/2002 | Storz et al. | 250/234 |
| 2008/0130093 A1 * | 6/2008 | Silberberg et al. | 359/298 |

OTHER PUBLICATIONS

Andresen, et al. "Time-multiplexed multifocal multiphoton microscope," Opt. Lett. 26:75-77 (2001).
Bewersdorf, et al. "Multifocal multiphoton microscopy," Opt. Lett. 23:655-657 (1998).
Crocker, et al. "Methods of digital video microscopy for colloidal studies," J. Coll. Inter. Sci. 179:298-310 (1996).
Diaspro, *Confocal and two-photon microscopy* (Wiley, New York, 2002).
Egner, et al. "Time multiplexing and parallelization in multifocal multiphoton microscopy," J. Opt. Soc. Am. A 17, 1192-1201 (2000).
Fittinghoff, et al. "Time-decorrelated multifocal array for multiphoton microscopy and micro-maching," Opt. Lett. 25:1213-1215 (2000).

(Continued)

*Primary Examiner* — Roy Punnoose
(74) *Attorney, Agent, or Firm* — Marshall, Gerstein & Borun LLP

(57) ABSTRACT

A rapid-sampling stochastic scanning multiphoton multifocal microscopy (SS-MMM) fluorescence imaging technique enables multiparticle tracking at rates upwards of 1,000 times greater than conventional single point raster scanning. Stochastic scanning of a diffractive optical element may generate a 10×10 hexagonal array of foci with a white noise driven galvanometer to yield a scan pattern that is random yet space-filling. SS-MMM may create a more uniformly sampled image with fewer spatio-temporal artifacts than obtained by conventional or multibeam raster scanning.

43 Claims, 6 Drawing Sheets

OTHER PUBLICATIONS

Jin, et al. "Correlating second harmonic optical responses of single Ag nanoparticles with morphology," J. Amer. Chem. Soc. 127:12482-12483 2005.

Kim, et al. "High-speed, two-photon scanning microscope," Appl. Opt. 38:6004-6009 (1999).

Sacconi, et al. "Multiphoton multifocal microscopy exploiting a diffractive optical element," Opt. Lett. 28:1918-1920 (2003).

Toussaint, Jr., et al. "Generation of optical vector beams using a diffractive optical element interferometer," Opt. Lett. 30:2846-2848 (2005).

Jureller, "Nonlinear and correlation microscopies for dynamics and function in heterogeneous systems," Ph.D. Dissertation, The University of Chicago (2006).

Dank, et al. "Two-Photon Laser Scanning Fluorescence Microscopy," Science 248:73-76 (1990).

Digman, et al. "Measuring Fast Dynamics in Solutions and Cells with a Laser Scanning Microscope," Biophysical Journal 89:1317-1327 (2005).

Jiang "Non-scanning Fluorescence Confocal Microscopy using Laser Speckle Illumination," The University of Nottingham, pp. 1-141 (2005).

Jureiler, et al, "Stochastic scanning multiphoton multifocal microscopy," Optics Express 14(8):3406-3414 (Apr. 17, 2006).

Levi, et al. "3-D Particle Tracking in a Two-Photon Microscope: Application to the Study of Molecular Dynamics in Cells," Biophysical Journal 88:2919-2928 (2005).

Oron, at al. "Scanningless depth-resolved microscopy," Optics Express 13(5):1468-1476 (2005).

* cited by examiner

STOCHASTIC SCANNING APPARATUS USING MULTIPHOTON MULTIFOCAL SOURCE

CROSS REFERENCE TO RELATED APPLICATIONS

The benefit under 35 U.S.C. §119(e) of U.S. Provisional Patent Application Ser. No. 60/818,195 filed Jun. 30, 2006, is hereby claimed, and its disclosure is hereby incorporated herein by reference.

SPONSORED RESEARCH

The invention was made with government support under CHE-0216492 awarded by the National Science Foundation. The government has certain rights in the invention.

FIELD OF THE DISCLOSURE

The present disclosure relates generally to imaging and, more specifically, to multiphoton microscopy imaging of a sample.

BACKGROUND OF RELATED ART

Measuring transport dynamics in temporally and spatially heterogeneous nano- and micro-scale systems (e.g., cargo vesicles in vivo) requires high-resolution and high-fidelity concurrent tracking of individual objects over large fields of view. Laser scanning confocal or multiphoton fluorescence microscopies are powerful approaches for such imaging and tracking. Yet, suitable systems, particularly those with spinning discs or resonant galvanometers, are often expensive, specialized, and closed "black boxes" that hinder operator innovation. These systems must, for example, have rapid scanning rates to avoid the spatiotemporal artifacts in the measured sample dynamics that arise from the laser scanning spatial response function.

Consider a raster laser scanning multiphoton fluorescence microscopy imaging process with a raster scanner (e.g. resonant or non-resonant galvanometer) and non-descanned detection: sweeping an excitation spot or pattern over a sample area in the conjugate plane of an array detector produces an image. The exposure time of that detector must be synchronized to the period of the raster scanner drive waveform. In particular, the exposure time must be synchronized to the period of the drive waveform for the slow axis. This introduces an asymmetry, as the fast axis is continuously sampled, while the slow axis is discretely sampled. As a result, raster scanning utilizes only a portion of the possible scanning power spectral bandwidth, limiting (non-resonant) full-field imaging rates to a few frames per second. Furthermore, no information is available about an area of a sample while the excitation beam is elsewhere. For processes with timescales comparable to or faster than the full frame rate of the raster scanner, especially those with wide fields of view, temporal and spatial aliasing artifacts result, due to the inability of the system to sufficiently resolve events over the entire sample.

To improve scanning efficiency, some have proposed multifocal multiplexing using two-dimensional patterns of excitation spots dithered within the periodic bounds of the array. Initial implementations of multiphoton multifocal microscopy (MMM), for example, utilized microlenses, cascaded beamsplitter arrays, and low-spot-density diffractive optical elements (DOE) to generate excitation patterns. DOE beamsplitters offer compactness, stability, efficiency, and uniformity. DOE throughput (~75%) is similar to microlens arrays without pinholes and allows producing a large number of beams (~100) with uniform intensity (<5% peak-to-peak variation). However, previous designs relied on conventional raster scanning and lead to oversampling at the edges of each unit cell due to the finite mechanical response of the scanner. Hence, the resulting images exhibited an undesirable, gridwork appearance. It is, therefore, desirable to maintain flexibility for the utilization of random access scanning modes, such as have been recently employed for measurement of intracellular transport, but in a system capable of accurate imaging over an entire sample region and without the bandwidth limitations of conventional raster scanners.

SUMMARY OF THE INVENTION

We demonstrate a rapid sampling stochastic scanning multiphoton multifocal microscopy (SS-MMM) approach that addresses the shortcomings of conventional systems. The SS-MMM enables high-speed uniform imaging and allows high-fidelity multiparticle tracking. The method includes using a DOE to generate an excitation beam array (e.g., a 10×10 array) arranged in a hexagonal lattice. This array may yield, for example, 100 beam foci at the objective focal plane that are scanned by an optical scanner, such as a galvanometer. Instead of driving the galvanometer with a conventional raster waveform, however, the galvanometer may be driven by a random signal source in the form of a "white noise" waveform, for example, resulting in a random scanning of the foci beams. With this stochastic, or random, scanning, as that term is used herein, the image may be sampled and "built-up" within a given integration time that determines the overall image fidelity, rather than at a set frame rate.

The resulting images may be evenly and symmetrically sampled for full-field scanning with an asynchronous frame readout (i.e. the detector and scan are not synchronized) 1000 times greater than conventional single beam rastering. Expensive specialized equipment is avoided as well as the artificial duty-cycle inefficiencies designed to account for unequal mechanical scanner residency times (e.g. electro-optic beam-blanking of the excitation at the edges of the scan waveform). As a result, imaging and tracking rates may be determined by the intrinsic fluorophore brightness, detector sensitivity and readout rate not by the scanner, for example.

The experimental results obtained were supported by Monte Carlo simulations of microsphere diffusion and SS-MMM imaging. The SS-MMM approach was demonstrated for high-resolution multiparticle tracking and imaging with multiphoton excitation, which has the advantages of deep confocality, low background, and reduced overall (primarily out-of-plane) photobleaching advantages. SS-MMM may therefore be a powerful technique for tracking intracellular cargo vesicles or other particles (e.g., microspheres or nanoparticles) in vivo and/or in vitro. Additionally, the stochastic scanning method is general and adaptable to, for example, one-photon confocal descanned systems.

In some examples, a method of imaging comprises: illuminating a sample with light of wavelength n, wherein the light illuminates the sample over a random path across a sample region; and continuously collecting fluorescent radiation over the sample region.

In other examples, a method of imaging a sample comprises: continuously randomly scanning a light beam as a plurality of foci light beams over a two-dimensional focal region at the sample; and detecting the resulting radiation from each of the foci light beams at the focal region of the sample.

In other examples, an apparatus for imaging a sample comprises: a light beam source producing a light beam comprising a plurality of spaced apart light beams; a scanner having an element disposed to receive the light beam and randomly scan the plurality of spaced apart light beams across a region of interest; and a focusing element disposed to focus the plurality of spaced apart light beams onto a focal region as a plurality of foci light beams.

DETAILED DESCRIPTION OF AN EXAMPLE

The present application demonstrates stochastic scanning multiphoton multifocal microscopy (SS-MMM) fluorescence techniques that may be used for high-speed imaging, such as of multiparticle tracking of fast dynamics over large fields of view.

In an example, a hexagonal array of 100 excitation foci generated from a DOE is described. Stochastically scanning the array across a focal region at a sample provides enhancement in sampling bandwidth and imaging uniformity versus raster scanning. Instead of using a single frequency necessarily well below the resonant frequency, the entire optical scanner (e.g., galvanometer) bandwidth may be used (with amplitude up to 3 kHz, 10× greater than the galvanometer resonant frequency). This approach allows >100-fold more temporal information to be obtained with more uniform coverage over a sample than simply overdriving a multifocal rastering waveform on a galvanometer. The limit is rarefication of sampling, which leads to sparsity in the image or "blinking" of objects from frame to frame. No hardware or software synchronization of the scan pattern to the CCD pixel clock is required. Therefore, inexpensive equipment may be used without modification to achieve similar performance to expensive and sealed commercial systems.

The SS-MMM techniques described may be used for biological tracking applications such as measuring the transport of intracellular cargo vesicles, proteins, molecules, cells, tissues, or introduced objects such as microspheres or nanoparticles. Similarly, the SS-MMM method is applicable to all tracking applications in physical, biological, chemical, and material systems where a detectable signal (e.g., fluorescence, luminescence, harmonic generation, scattering, absorption, n-wave mixing, phase shifts, etc.) is generated by the excitation array. Although certain examples are described for two-dimensional application, the SS-MMM technique may be extended to three-dimensional volumes and four-dimensional volumes, when considering time.

Figure 1:
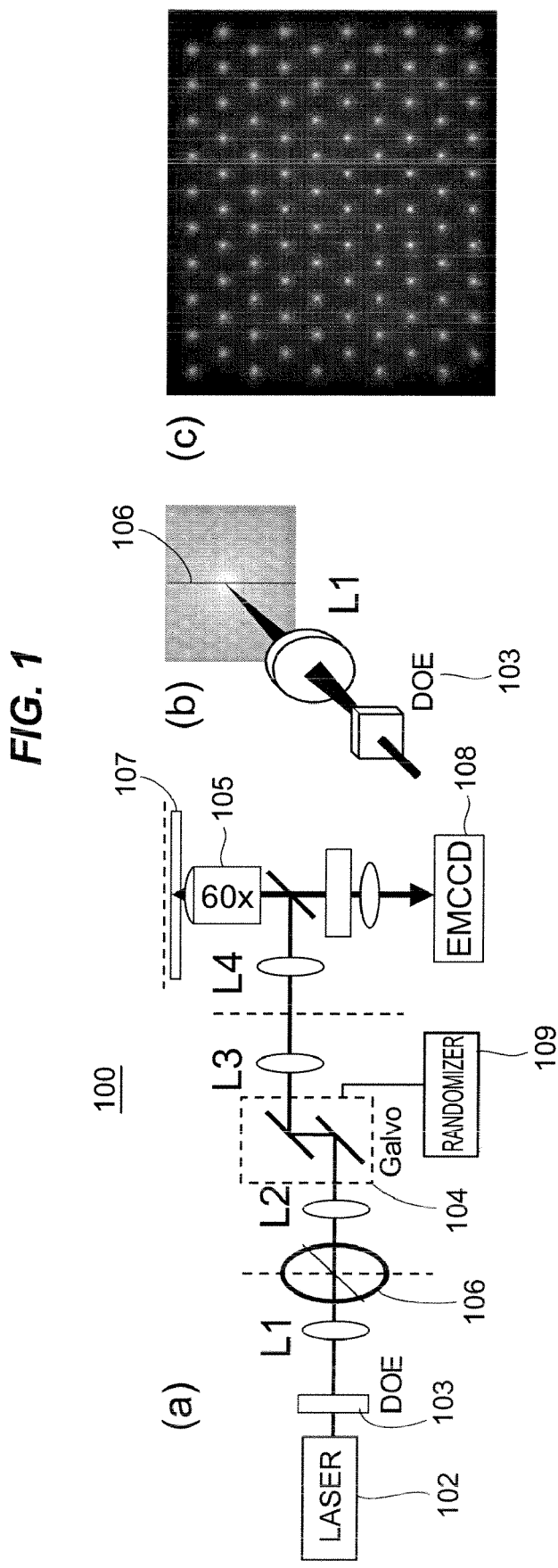
FIG. 1(a) illustrates an example stochastic scanning multiphoton microscopy apparatus.
FIG. 1(b) illustrates a plurality of beams generated as a 10×10 array from the apparatus of FIG. 1(a).
FIG. 1(c) illustrates a color two-photon fluorescence image (in black and white) of the foci array of FIG. 1(b).

An example SS-MMM system 100 is shown in FIG. 1(a). The system 100 includes a nonlinear optical (i.e. 2-photon) microscope for multiphoton fluorescence detection. In operation, a laser source 102 produces a light beam to be scanned across an image. In an example, the laser source 102 is a tunable Ti:Sapphire laser source 102 (e.g., a Spectra-Physics Mai Tai) producing 70 fs duration pulses at 930 nm. The laser source 102, for example, was used to generate the 2-photon fluorescence at the focal region, e.g., focal plane, of a 1.2 NA 60× water immersion apochromat objective 105 (Olympus UPLSAPO 60XW) mounted on an inverted microscope (Nikon TE2000E) (not shown). It will be appreciated that other types of laser sources may be used, including pulsed or continuous laser sources with external means for controlling the rate at which the image plane is illuminated, e.g., through mechanical choppers, pulse pickers, or similar optical elements. Furthermore, the particular wavelength of laser source 102 may be different, although preferably that wavelength is such as to generate 2-photon absorption in the sample, without post-laser source wavelength conversion. Example wavelength ranges for the laser source 102 would be from 200 nm to 2 μm.

The pulses from the Ti:Sapphire laser source 102 may be passed through a dispersion pre-compensation element in the form of a BK7 Brewster-cut prism line (not shown) and through a spatial filter for beam cleanup (not shown). The pulses are then communicated to a DOE 103. In the illustrated example, the DOE 103 is part of the coherent light beam source and receives in the input light beam from the laser source 102 and produces a plurality of spaced apart light beams. The DOE 103 may produce a 10×10 hexagonal array of excitation beams, with a measured generation efficiency of 75% and <5% variation in beam intensity, for example. The period of the two-dimensional diffraction grating comprising the DOE 103 may be, by way of example, 219 μm. The hexagonal geometry and resultant even inter-beam spacing allows optimal sampling and imaging efficiency. In an example implementation, a customized DOE from Holoeye Photonics AG of Berlin, Germany, was used to produce a hexagonal output pattern with a 20 cm focal length. Although a hexagonal array pattern was used, it will be understood that other patterns of arbitrary number and spacing may be used instead. Additionally, multiple non-diffractive beamsplitters or any other methods of generating multiple replica beams such as microarrays of lenslets may be used.

A telescope element formed by lenses L1 and L2 is used (e.g., a telescope constructed with near-IR achromats (L1, f.l.=20 cm and L2, f.l.=35 cm)) in a standard 4-f configuration. The telescope element images the output pattern from the DOE 103 onto the face of a galvanometer optical scanner 104. The residual undiffracted beam at the zero order is designed to occur in an interstitial space and is mechanically blocked with a wire element 106 at the focus of the telescope after lens L1, also the first conjugate plane of the sample plane (FIG. 1(b)). FIG. 1(b) shows the imaged DOE pattern after the element L1.

The pattern from the DOE 103 is scanned across the field of view by the galvanometer scanner 104, which in the illustrated example comprises a two-mirror closed-loop galvanometer (e.g., a Cambridge Tech 6650). The galvanometer is a type of optical signal scanner that in the discussed examples acts as randomizer for randomly scanning a two- or three-dimensional sample region. Using a galvanometer allows one to scan the hexagonal (or other DOE patterned) beam from the DOE 103 for what will be random or near random scanning across the focal region. Various types of galvanometers are available, including moving magnet and moving coil galvanometers, and are often in a closed loop control configuration. Typically these galvanometers rely upon capacitive detection techniques to finely control position and movement of the galvanometers. More generally, many optical scanners may be used, including electrically controlled, mechanically controlled and piezoelectrically controlled scanners. Beyond galvanometers, additional examples include spatial light modulators, electro-optic deflectors, and acousto-optical deflectors. Yet other examples include voice coil mirror pairs. The SS-MMM method is applicable to all types of mechanical, optical, and electrical scanners. For the illustrated example, the galvanometer scanner 104 may have a 286 Hz resonant frequency (selected for stability and accuracy) and may be driven by a random noise generator 109, such as triangular raster or white noise waveforms synthesized by a NI-6052E DAQ card, i.e., a standard data acquisition card. The random noise generator 109 may be an electrical noise signal generator or a mechanical noise signal generator.

In conventional raster scan mode, fast axis scan rates must be limited to under 100 Hz to avoid mechanical lags and therefore the overall imaging rates (slow axis) are limited to 1-2 fps. With the stochastic scanning applied herein, imaging rates are not limited in this way.

The optical train is completed with a near-IR achromat scan lens (L3, f.l.=15 cm) and tube lens (L4, f.l.=20 cm) leading to the primary objective 105, which images the output pattern from the DOE 103, as randomized by the galvanometer 104 onto a sample 107. The sample 107 may be illuminated at a focal plane at the top of substrate or material, yet in other examples, the sampled layer is within such a substrate, i.e., between upper and lower surfaces of a sample material. The sample may include a carrier material, a marker material, and a measurable agent corresponding to the marker material. The wavelength of the laser source 102 would typically not be resonant with the carrier material (or at least substantially non-resonant) and would correspond to an energy sufficient to produce multiphoton fluorescence of the marker material. This would allow the SS-MMM technique to continuously collect fluorescent radiation over the two-dimensional sample region from the marker only. As described herein, the fluorescence radiation may be collected from the sample region separately from the pulse and scatter wavelengths.

Various techniques may be used to collect the multiphoton fluorescence from the illuminated sample. In an example implementation, multiphoton fluorescence generated in the sample was epi-detected, separated from the scattered laser light with a green HQ525/50 m bandpass filter and E700SP2 NIR blocking filter (Chroma). Epi-fluorescence was then imaged onto a 1000×1000 pixel TE-cooled EMCCD camera 108 (Andor DV885) with 100× total magnification. Effective back-projected pixels are 80 nm square. While this example implementation was used, other techniques for multiphoton fluorescence collection and imaging will be known.

The configuration of FIG. 1(a) may be used to scan multiphoton fluorescence from a sample region at very fast scan rates over an integration time period. As outlined in the table below, scan rates of 10 scans per second, 100 scans per second, and 1000 scans per second may be achieved, for example. Whereas, scanning of the (multi-foci) light beam may be performed continuously over a time period, detecting the fluorescence radiation may be performed periodically over an integration time period of approximately the inverse of the number of frames per second or faster. Unlike conventional raster scanning, the scanning and detection rates are asynchronous and need not be related or synchronized. Such scan rates can be quite useful in measuring movements of chemical and biological elements within the sample region, for example, during marker fluorescence tracking.

FIG. 1(c) shows a 2-photon fluorescence image of the hexagonal array of excitation foci at the sample focal plane 107 with a solution of Rhodamine 6G at the sample plane 107. Foci are separated by 6 μm to prevent adverse interference effects. The average power of the pattern is adjustable with neutral density filters so that individual foci at the sample plane have 0.5-10 mW each.

Figure 4:
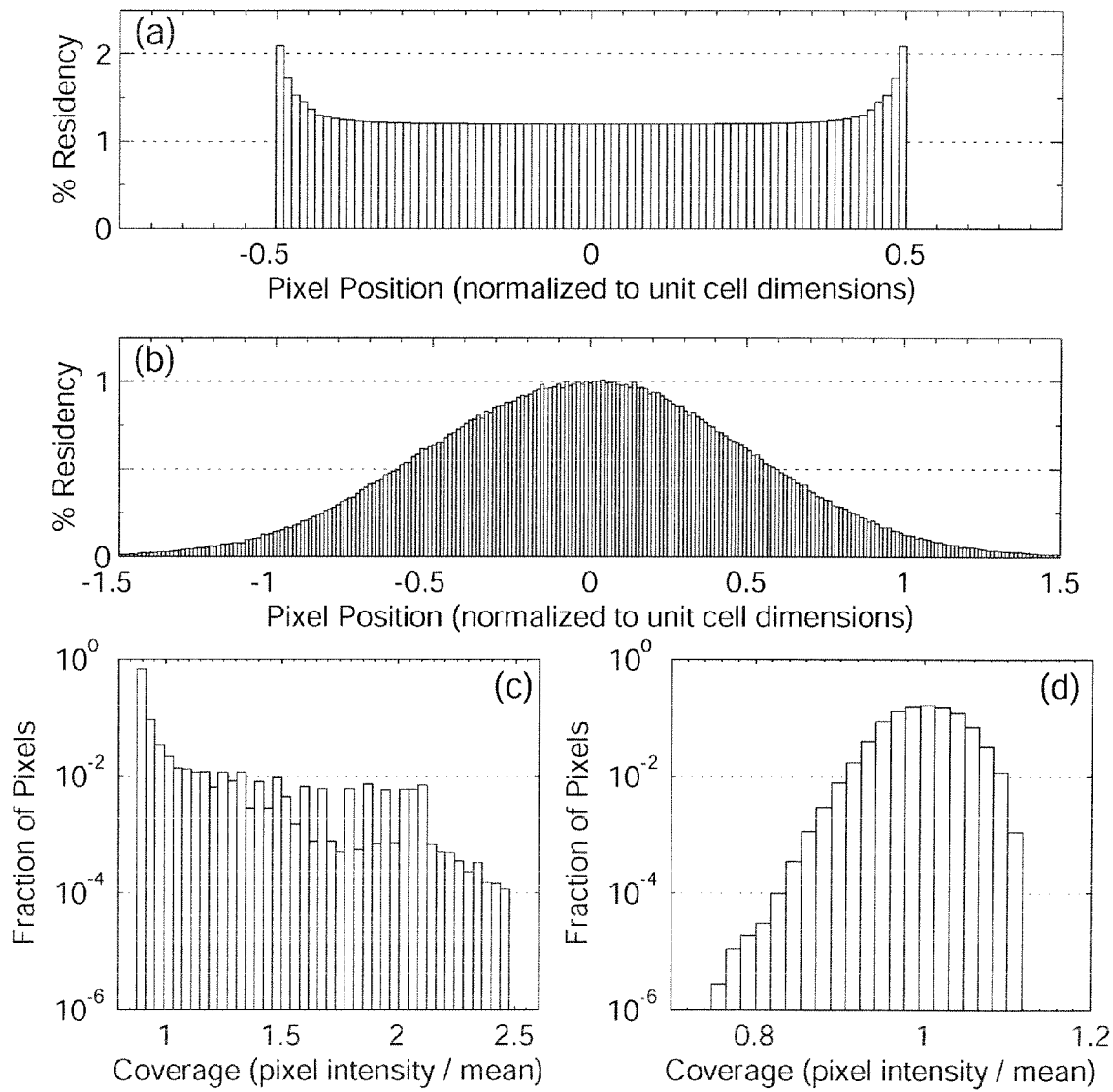
FIG. 4(a) illustrates a histogram of simulated fast axis residency times for a raster scan and showing outer edge oversampling.
FIG. 4(b) illustrates a histogram of simulated fast axis residency times for a stochastic scan.
FIG. 4(c) illustrates a histogram of scanning coverage for simulated full images at 1 fps for a raster scan.
FIG. 4(d) illustrates a histogram of scanning coverage for simulated full images at 1 fps for a stochastic scan.
FIG. 4(e) illustrates an intensity distribution of the scan pattern in terms of spacing distance between adjacent foci in a focal plane at a sample region.
Figure 4E:
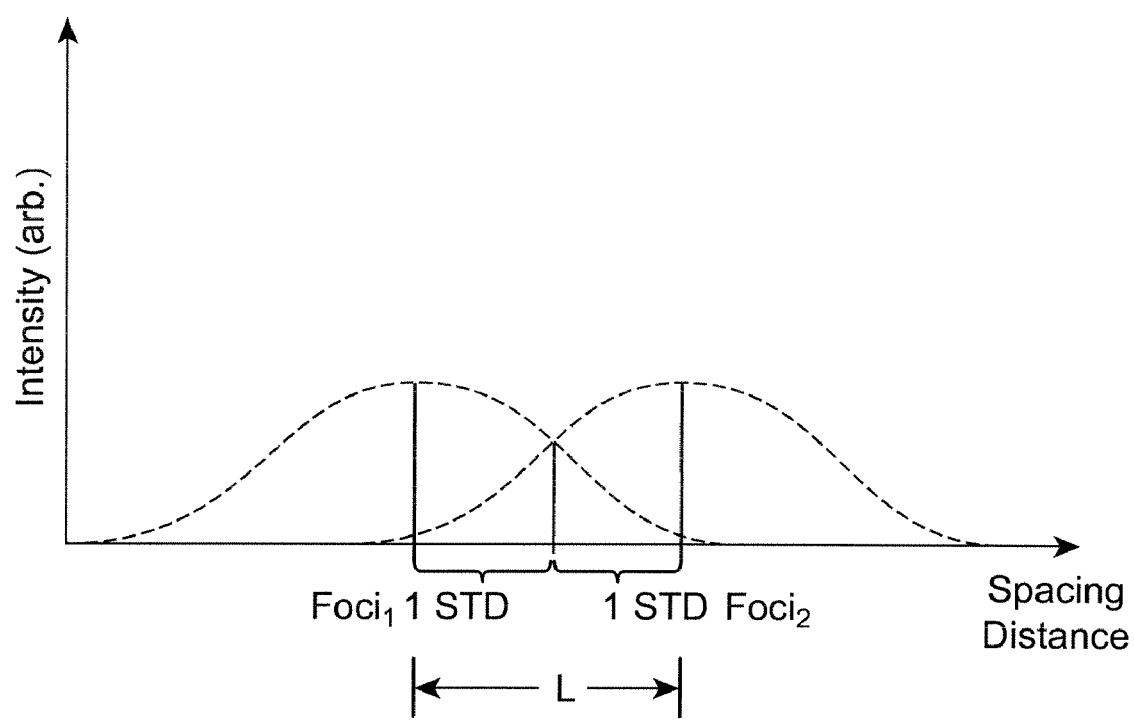

The spacing distance between adjacent foci may be set to approximately one or two standard deviations of the Gaussian profile of the illumination produced by the scan pattern of any single one of the plurality of foci light beams (see FIG. 4(e)). The spacing distance between adjacent foci light beams may be adjusted by adjusting the optical elements such as the lenses or mirrors (for example L2 and L3 in the apparatus figure) or choice of a different DOE or other beamsplitter element.

Example SS-MMM techniques were used to measure the diffusion of 500 nm diameter yellow-green fluorescent microspheres (Duke) in aqueous solution between two coverslips at the sample and separated by a 100 μm gasket. The Stokes-Einstein relation gives an expected diffusion coefficient D=0.88 μm$^2$/s.

Figure 2:
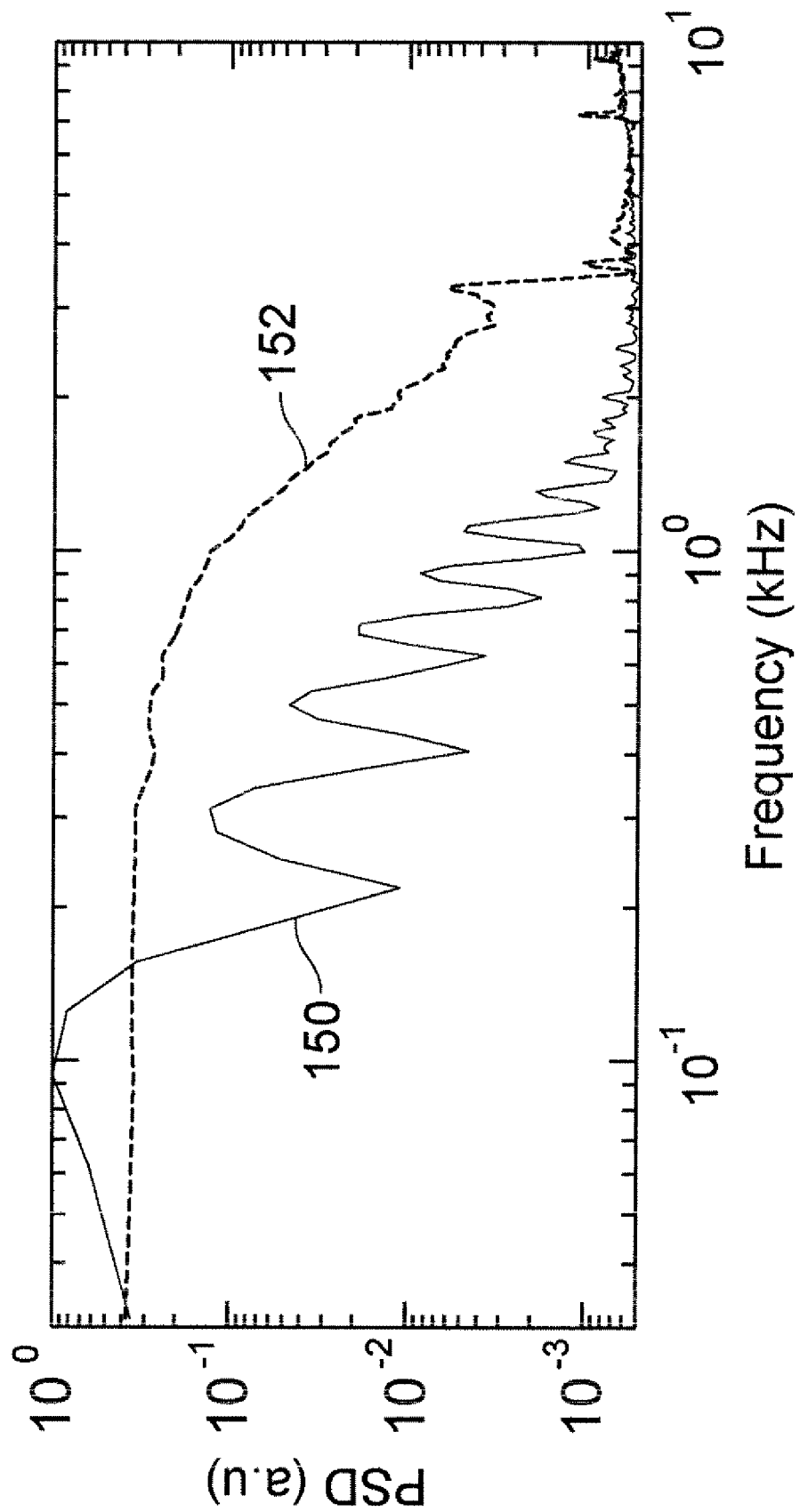
FIG. 2 illustrates a log-log plot of a measured galvanometer response power spectral density for a random noise source and a raster waveform course.

FIG. 2 shows the galvanometer response power spectral density measured with a spectrum analyzer (SRS SR760). Curve 150 results from a 100 Hz raster scan drive waveform while curve 152 results from a white noise drive waveform that utilizes the full 333 KHz bandwidth of the DAQ. This latter response is pertinent for SS-MMM and reflects the total mechanical bandwidth available from the galvanometer scanner 104. The curve 152 is substantially flatter and extends to much higher frequencies than the raster response curve 150. The odd harmonic components of the raster response curve 150 result from the approximation of a triangular wave drive waveform, with dominant contributions from the edges of the trajectory, i.e., the reversal points. Triangular drive waveforms are preferred to simple square and step drive waveforms due to the minimization of stop-start impulses to the scanner.

Stochastic scanning enables high-frequency content at all points in the scan pattern, while raster scanning contains high-frequency content primarily at the edges of the scan pattern. Therefore stochastic scanning is mechanically more efficient than rastering at a sub-resonant frequency.

Figure 3:
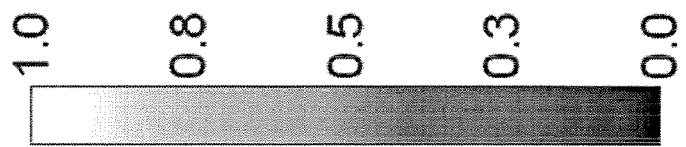
FIG. 3(a) illustrates a single frame two-photon fluorescence raster scan image of a packed monolayer of 500 nm diameter microbeads at 1 fps and showing a brickwork pattern from oversampling.
FIG. 3(b) illustrates a single frame two-photon fluorescence stochastic scanning multifocal fluorescence image of the same area shown in FIG. 3(a).
Figure 3:
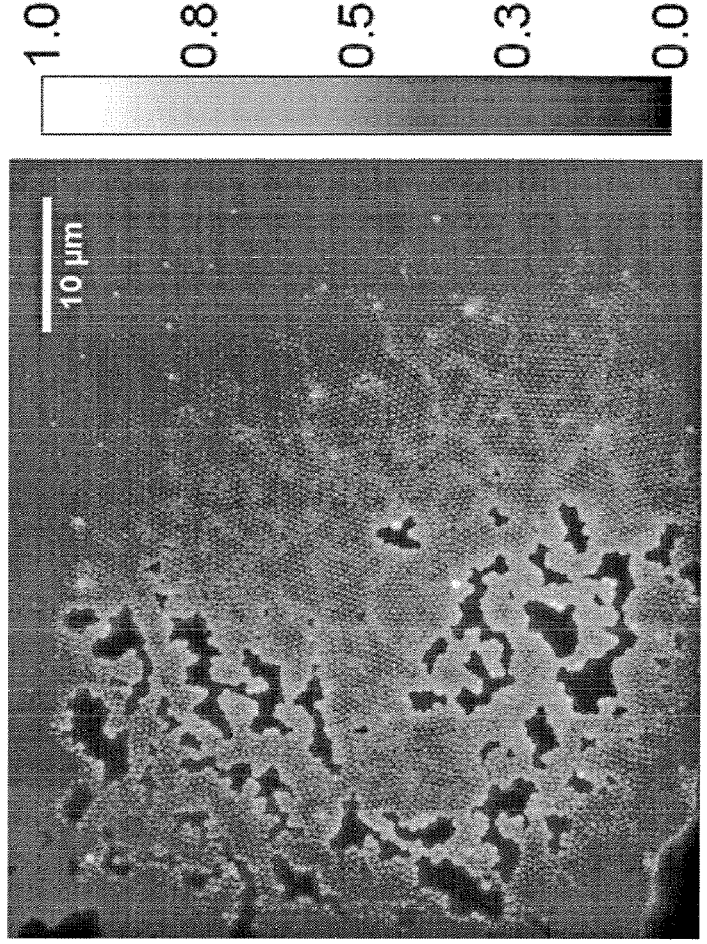
Figure 3:
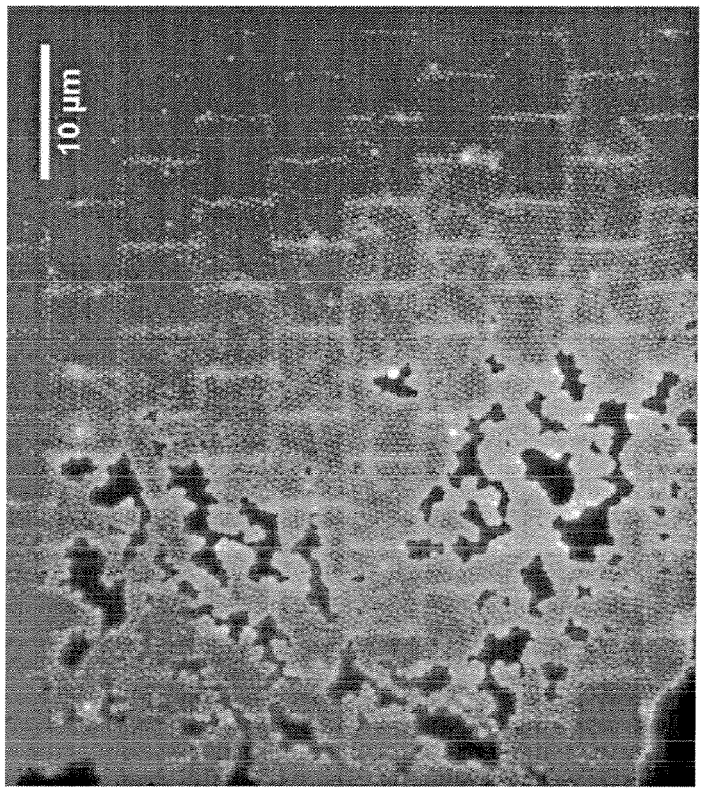

FIG. 3(a) shows a single frame 2-photon fluorescence image of a monolayer of 500 nm diameter fluorescent microspheres acquired with raster scanning at 1 fps. Boundaries between periodic replica cells are clearly over-sampled and are observed as bright edges of the single beam scan area. The result is the brickwork like pattern. The slow axis edges (horizontal) are deemphasized versus the fast axis edges (vertical), but still noticeable for this technique. This relatively slow imaging rate (1 fps) represents the best-case-scenario for raster scanning; imaging at faster rates will only increase the observed artifacts.

FIG. 3(b) shows a single frame 2-photon fluorescence image of the same area shown in FIG. 3(a) obtained by stochastic scanning. The sampling is much more uniform and the image does not display the edge sampling artifacts.

The DOE acts as a spectrally dispersive element that can spatially broaden the foci at the sample focal plane. Calculated spatial dispersion of the 10 nm spectral bandwidth pulses ranges from 91 nm FWHM for the 1st order spots to 460 nm FWHM for the highest order spots at the pattern edge. This estimate includes a 2.3× magnification of the DOE 103 from the two telescopes (L1, L2, L3 and L4). These values are less than the 460 nm FWHM linear diffraction-limited illumination focus for the 930 nm excitation pulses of the laser source 102 and create a <√2 increase in a spot size at the pattern's edge. The overall effect decreases the instantaneous peak power found in the foci of each light beam and thus reduces the 2-photon fluorescence. In practice, this effect was small and confined to the edge of the pattern. Identical reductions in intensity toward the edge of the image are observed for both raster and stochastic scanning in FIG. 3.

A greater reduction at the very edges of the stochastic scanning full field of view also reflects the reduced illumination resulting from the outermost unit cells of the scan pattern, where the next unit cell does not exist and cannot contribute to smoothing the pattern boundaries. As a result, while the entire sample may be illuminated with the multi-foci pattern from the DOE 103, in some examples only a central portion, for example, the central 8×8 (even 9×9) pattern region, of the image may be uniformly illuminated. In response, in some examples, the fluorescence collection may therefore focus on only a portion of the illuminated foci at the sample, such that lower intensity foci are not used for fluorescence collection. Alternatively, in some examples, the entire multi-foci plane is imaged and the fluorescence collection apparatus may detect lower intensity foci and compensate for the lower intensity (e.g., through normalization) or may discard such data. Various techniques for intensity measurement, and normalization, or blocking may be done digitally through a processor and data analysis, but such techniques may be done in the mechanical or optical domains as well.

Monte Carlo simulations (written in Matlab) of the imaging process were undertaken to better quantify the SS-MMM technique. Experimental parameters (e.g., the galvo mechanical response, pixel size, beam waist, excitation spot spacing and field of view) were included to yield realistic data that was validated by direct comparison to experimental measurements.

The SS-MMM technique is capable of very high frame rates (video and beyond) and the simulations allow modeling these conditions and extrapolation to higher imaging rates. A 10 MHz readout rate for an EMCCD may limit non-binned full-frame acquisition rates to 9 fps. Other fast readout rate CCDs or other optical detection techniques may be used to achieve scan rates of at least 10 fps, for example, at least 100 fps or at least 1000 fps. Alternatively, faster scan rates could be achieved through detection of only a sub-area of the image, at the expense of the large field of view covered by the excitation array.

FIGS. 4(a) and 4(b) show histograms of calculated fast axis pixel residence times within one unit (bin width=1 pixel) of the periodic multifocal array for raster (a) and stochastic (b) scans at 1 fps. Both axes are sampled equivalently rapidly for stochastic scanning with a bandwidth advantage as stated above. Raster scanning clearly oversamples the edges even at low speeds. Stochastic scanning yields nearly the inverse; the sampling is more uniform and mostly in the center of the unit cells. This sampling profile allows for an evenly sampled composite image when combining contributions from each part of the excitation array. The excursions outside the array unit cell serve to better blend each area with its neighbors. Conversely, raster scanning oversamples the unit cell edge and results in a gridwork effect. The advantages to stochastic scanning over raster scanning will be even greater at higher (overdriven) frequencies.

A metric was used to quantify the quality and extent of scanning "coverage," i.e., the distribution of total excitation dosage a given sample position or conjugate EMCCD pixel receives due to the beam scanning trajectory. The coverage may be quantified in a histogram of pixel intensity values in the scan region normalized by the value expected for completely uniform illumination, i.e., the mean pixel intensity averaged over the whole image. The histogram of a perfect, uniformly covered scan pattern would yield a delta function at 1. The relative standard deviation of the coverage distribution, describing the width of the histogram, can then be calculated as the standard deviation of the pixel intensities divided by the mean intensity value. A narrow relative standard deviation indicates the uniformity of coverage. In this way, histograms for scan patterns with different mean values may be directly compared and used to quantify the smoothness and completeness of scanning coverage.

FIGS. 4(c) and 4(d) show histograms of coverage values (pixel intensities normalized by the mean image intensity) calculated from images generated by simulations of multifocal (c) raster and (d) stochastic scanning trajectories at 1 fps. The areas of the histograms are normalized to one, so that they may be read as the fraction of pixels with a given coverage. The width of the stochastic scanning histogram is much narrower and distributed around 1, indicating a high degree of image scanning uniformity. The raster histogram exhibits significant non-uniformity. The higher coverage values indicate some pixels are oversampled, for example, up to 2.5 times the average illumination. This is a signature of oversampling of the edges of the scan unit cell. The stochastic histogram does display a small tail of undersampling, resulting from the outermost edges of the scan pattern where the next unit cell to "blend" the coverage does not exist, but otherwise provides a cleaner more uniform response.

Table 1 gives the mean pixel intensities on a scale of zero to unity and the relative standard deviations of additional histogram distributions (not shown) at representative frame rates.

TABLE 1

Imaging simulation coverage results

| Scan type | fps | Mean Intensity | Relative Std Dev |
|---|---|---|---|
| Stochastic | 1000 | 0.047 | 1.17 |
| Stochastic | 100 | 0.278 | 0.362 |
| Raster | 100 | 0.129 | 0.801 |

TABLE 1-continued

Imaging simulation coverage results

| Scan type | fps | Mean Intensity | Relative Std Dev |
|---|---|---|---|
| Stochastic | 10 | 0.692 | 0.115 |
| Raster | 10 | 0.537 | 0.154 |
| Stochastic | 1 | 0.901 | 0.040 |
| Raster | 1 | 0.407 | 0.257 |

For equivalent conditions, stochastic scanning produces more evenly sampled images with narrower distributions; i.e., the mean values are higher and the relative standard deviations are smaller. Importantly, all stochastically scanned pixels have non-zero values until frame rates exceed 100 fps. This means that the excitation beam illuminates each pixel and that there are no "holes" in the scanning trajectory. Beyond this rate (e.g. 1000 fps) there is a probability that a pixel will not be visited, creating a blinking effect from frame to frame. This specific restriction does not arise from the SS-MMM method, but from the particular galvanometer used in the example demonstration. Faster scanners (with more bandwidth) will allow higher rates (e.g. greater than 1000 fps) to be achieved. The SS-MMM is general and has no inherent speed restrictions but is limited by the experimental equipment (e.g. scanners, detectors, optics etc) chosen in the implementation. These observed temporal artifacts would be similar to those encountered with much slower (~1 fps) raster scans. Conservatively, estimating approximately 100 fps as a benchmark level for stochastic scanning with the particular galvanometer setup used gives a 1,000-fold improvement over conventional single-beam rastering.

FIG. 4(e) illustrates the intensity distribution profiles for the scanning trajectory for two adjacent foci, where the intensity distribution has been adjusted (for example through repositioning of one or more optical elements or modification of the drive waveform) such that the physical spacing distance, L, corresponds to an intensity distribution spacing distance of 2 standard deviations (STD) of each profile as shown.

The spacing distance between adjacent intensity distribution profiles of the foci beams may be spaced apart such that they are approximately, but not limited to, two standard deviations apart. Other arbitrary spacing may be chosen in conjunction with selection of other imaging, optical, or mechanical parameters. In some examples, that spacing distance resulted in 6 μm spacing distances, peak to peak.

The stochastic scanning methods may be used in numerous different applications. Applications include, but are not limited to, single particle and/or object tracking, multi-particle or and/or object tracking, high and low speed imaging, particle and/or object identification and localization, fluctuation measurements.

Figure 5:
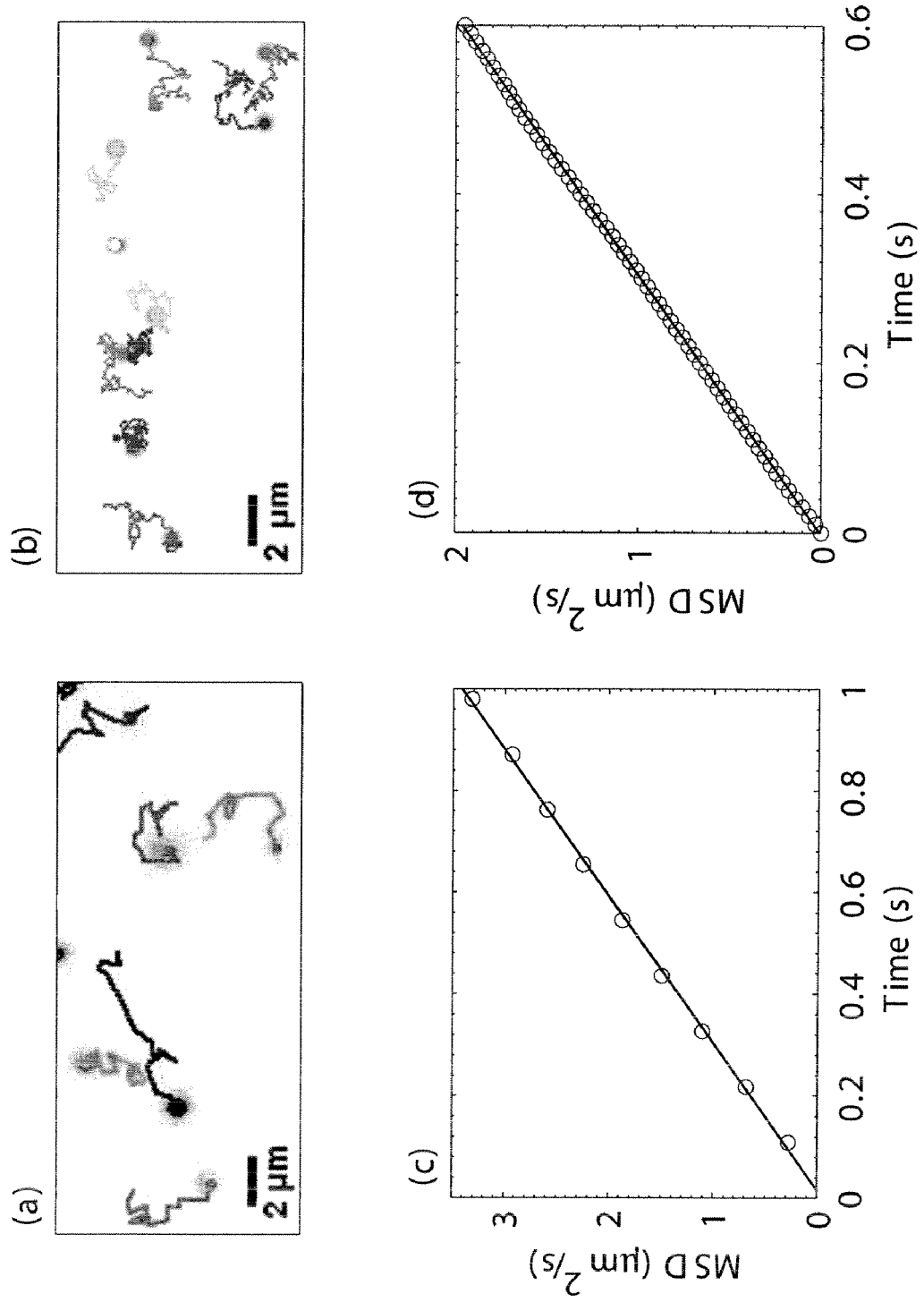
FIG. 5(a) illustrates a representative experimental microsphere trajectory measured with a stochastic scanning multifocal multiphoton microscopy apparatus at 9 fps.
FIG. 5(b) illustrates a representative simulated microsphere trajectory measured with a stochastic scanning multifocal multiphoton microscopy apparatus at 100 fps.
FIG. 5(c) illustrates a mean square displacement (MSD) from the experimentally measured trajectories in FIG. 5(a).
FIG. 5(d) illustrates a MSD from the simulated trajectories in FIG. 5(b).

FIG. 5(a) shows a portion of an image of 500 nm diameter fluorescent microspheres diffusing in aqueous solution. The image was acquired at a scan rate of 9 fps with SS-MMM. Centroid particle tracking analysis of the images allows calculation of the mean square displacement (MSD). For two-dimensional diffusion (appropriate for bead trajectories that stay within the optically sectioned focal plane), the fitted slope of the MSD should equal 4 D. FIG. 5(c) shows the measured average MSD (circles) of the microspheres. A linear fit (solid line) yields a diffusion coefficient of 0.87 $\mu m^2/s$, in very good agreement with the expected value of D=0.88 $\mu m^2/s$.

FIG. 5(b) shows a simulated stochastic scanning image of 500 nm diameter fluorescent microspheres diffusing in aqueous solution at 100 fps. The diffusion coefficient used in the Monte Carlo simulation was 0.82 $\mu m^2/s$. FIG. 5(d) shows the measured average MSD (circles). A linear fit (solid line) gives 0.82 $\mu m^2/s$ as the diffusion coefficient. Particle trajectories and transport are still measured with high fidelity at 100 fps, unreachable with conventional single beam raster scanning.

It will be appreciated by persons of ordinary skill in the art that the stochastic scanning techniques herein are not limited to the example implementations described above. The optical scanner, for example, is described as two-mirror galvanometer which may use voice coils as drivers for the mirror pair. The galvanometer may instead be electro-optically controlled, acousto-optic controlled, mechanically controlled using other drivers, a piezo-electrically controlled mirror assembly, or a spatial light modulator (SLM). Other optical scanners that may be imparted with a randomizing operation on the incident plurality of foci light beams may be used instead.

Furthermore, it will be appreciated that these techniques are general and may be used in various imaging and detection techniques and are not limited to multiphoton absorption systems. Furthermore, the techniques are not limited to a particular type of microscopy or to microscopy at all. Examples of microscopy applications include (but are not limited to) phase, dark field, confocal, interferometric, standing wave, reflectance, fluorescence, nonlinear, multi-beam, wavefront coded, closed-loop, open-loop, differential, time-resolved, scattering, Raman, vibrational, dynamic, sub-diffractive, wide-field, interference, polarization, fluctuation, multi-color, vector-beam, and bright field microscopy. Single photon applications, such as single photon confocal microscopy and those (but not limited to) described immediately above, may also be implemented. Excitation sources that may be used include (but are not limited to) continuous and pulsed examples of lasers, light emitting diodes (LED), superluminescent LEDs, lamps, filaments, optical fibers, and other sources of electromagnetic radiation. Various cell, tissue, biological, chemical, physical, material, and nanoscale detection modalities may benefit from the described techniques. Further linear and nonlinear microscopy methods going beyond the diffraction limit may also be used, such as those benefiting from point spread function engineering and the use of vector beams. Applicability exists to all non-microscopy techniques that require particle and/or object tracking or scanning imaging and detection capabilities The techniques described herein may be extended to three-dimensional imaging by acquiring a succession of two-dimensional images (i.e. slices) separated along the third dimension, typically (but not limited to) the axial z-axis. The slices may then be reconstructed into a three dimensional image. Separation along the third dimension may be achieved by either moving the sample or changing the focal plane of the excitation light focused by the objective. The former may be achieved with a movable sample stage (e.g. micrometer, motorized, piezo, galvanometer driven) while the latter may be achieved by a movable objective or adjusting optics (e.g. lenses, mirrors) in the optical assembly. The end result of either approach is to shift the detection plane in the sample along the third dimension.

Furthermore, SS-MMM may be extended to simultaneous holographic "volumetric" imaging without acquiring successive two-dimensional images by using arbitrary three dimensional patterns of focal spots as could be created by a designed DOE or other beamsplitter element as described above. Similarly, an interferometer or other holographic element or instrument may be used to generate arbitrary and or detect three dimensional excitation patterns.

Three-dimensional imaging may also be achieved by use of a three-dimensional array detector, interferometer, or detector(s) sensitive to phase delays arising from detected light above or below the primary objective detection plane. For example, this could be realized by using multiple detectors, each sensitive to a specific two-dimensional plane separated along the third z-axis dimension. Furthermore, descanned detection with or without confocal pinholes would naturally allow time-resolved three-dimensional detection.

Above examples are described with a scanning system driven by a random or pseudo random positioning signal. Such a signal may be considered to be a "noise" signal. The demonstrated driving signal is a "white noise" signal meaning that the frequency power spectral density of the signal is flat and contains equal amplitudes of all frequencies. In the time domain, this means that all potential moves directed by the random positioning signal are equally probable and uncorrelated with the previous value of the signal and therefore the positioning is directed without bias.

The random positioning signal may also be "colored noise" in that the frequency power spectral density of the signal is not flat and contains varying amplitudes of frequencies bands. Examples include white, pink noise, red noise, blue noise, and brown noise. An appropriate filter, for example, may be used to transform white noise into another color of noise.

The mechanical scanner used has a finite frequency response based on its mechanical construction and composition. Driven by white noise, it therefore acts as a filter, and only responds linearly to frequencies in the drive signal for which it is physically capable (i.e., the power spectral density bandwidth in FIG. 2.) The most efficient random drive waveform would then be the inverse of its frequency response bandwidth, so that the produced scanning behavior would be absolutely flat in the frequency domain.

Although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalence.

What we claim is:

1. A method of imaging comprising:
   illuminating a sample with light of wavelength n, wherein the light illuminates the sample over a random path across a sample region; and
   using a detector to continuously collect a resulting radiation signal from the sample region.

2. The method of imaging of claim 1, wherein the resulting radiation signal is radiation having a wavelength of approximately n/x, wherein x is an integer.

3. The method of imaging of claim 1, wherein the resulting radiation signal is radiation having a wavelength greater than n.

4. The method of imaging of claim 1, wherein the resulting radiation signal has a wavelength approximately equal to n.

5. The method of imaging of claim 1, wherein the light is multifocal light.

6. The method of claim 5, wherein the multifocal light is arranged in a two-dimensional pattern across the sample region.

7. The method of claim 5, further comprising adjusting a spacing distance between adjacent foci of light such that each foci of light is spaced apart from each adjacent foci of light by approximately two standard deviations of the profile of an illumination produced at any one of the foci of light.

8. The method of claim 1, further comprising continuously collecting radiation over an integration time period corresponding to a scan rate of at least approximately 10 scans per second.

9. The method of claim 1, further comprising coupling the light into an optical signal randomizer for randomly scanning the two-dimensional sample region.

10. The method of claim 9, wherein the optical signal randomizer is a galvanometer driven by a white noise signal.

11. The method of claim 1, further comprising setting intensity of the light.

12. The method of claim 1, wherein illuminating the sample and collecting the radiation are asynchronized to one another.

13. The method of claim 1, wherein the light has a wavelength between approximately 200 nm and 2 μm.

14. The method of claim 1, wherein the sample comprises a carrier material, a marker material, and a measurable agent corresponding to the marker material, wherein the wavelength n is substantially non-resonant with the carrier material and which produces multiphoton fluorescence of the marker material, wherein continuously collecting fluorescent radiation over the two-dimensional sample region comprises optically separating the fluorescence radiation collected from the sample region.

15. A method of imaging a sample, the method comprising:
    continuously randomly scanning a light beam as a plurality of foci light beams over a two-dimensional focal region at the sample; and
    using a detector to detect the resulting radiation signal from each of the foci light beams at the focal region of the sample.

16. The method of claim 15, wherein the resulting radiation signal is multiphoton fluorescence radiation.

17. The method of claim 15, wherein the resulting radiation signal is single photon fluorescence radiation.

18. The method of claim 15, further comprising:
    coupling the light beam into a diffractive optical element to form the plurality of foci light beams;
    coupling the plurality of foci light beams into a random optical signal scanner; and
    focusing the plurality of foci light beams within the sample.

19. The method of claim 18, wherein the random optical signal scanner is a galvanometer, the method further comprising driving the galvanometer with a noise signal for randomizing the light beam.

20. The method of claim 19, wherein the noise signal is a white noise signal.

21. The method of claim 18, wherein the random optical signal scanner is a spatial light modulator.

22. The method of claim 18, wherein the random optical signal scanner is an electro-optic deflector or acousto-optic deflector.

23. The method of claim 15, wherein the plurality of foci light beams each have a wavelength of n, wherein detecting the resulting radiation signal comprises detecting radiation at a wavelength of n/x, where x is an integer.

24. The method of claim 15, wherein detecting the resulting radiation signal comprises detecting radiation at a wavelength greater than n.

25. The method of claim 15, wherein detecting the resulting radiation signal comprises detecting radiation at a wavelength equal to n.

26. The method of claim 15, wherein detecting the resulting radiation signal from the focal region comprises detecting radiation at a scan rate of at least approximately 10 scans per second.

27. The method of claim 15, wherein the plurality of foci are in an arrayed pattern.

28. The method of claim 15, further comprising adjusting a spacing distance between adjacent light beams of the plurality of foci light beams such that each of the plurality of foci light beams is spaced apart from each adjacent of the plurality of foci lights by approximately two standard deviations of the profile of an illumination produced at any one of the plurality of foci light beams.

29. The method of claim 15, further comprising adjusting a spacing distance between adjacent foci of the plurality of foci.

30. The method of claim 15, wherein scanning the light beam and detecting the resulting radiation signal are asynchronized to one another.

31. The method of claim 15, wherein scanning the light beam is performed continuously over a time period, and where detecting the resulting radiation signal is performed periodically over an integration time period of approximately 1/the number of frames per second or faster.

32. The method of claim 15, wherein the light beam has a wavelength between approximately 200 nm and 2 μm.

33. An apparatus for imaging a sample, the apparatus comprising:
   a light beam source producing a light beam comprising a plurality of spaced apart light beams;
   a scanner having an element disposed to receive the light beam and randomly scan the plurality of spaced apart light beams across a region of interest; and
   a focusing element disposed to focus the plurality of spaced apart light beams onto a focal region as a plurality of foci light beams; and
   a detector to detect the resulting radiation signal from the sample region.

34. The apparatus of claim 33, wherein the light beam source comprises a light source and a diffractive optical element for forming the plurality of spaced apart light beams.

35. The apparatus of claim 33, wherein the scanner comprises:
   a galvanometer; and
   a random noise signal generator.

36. The apparatus of claim 35, wherein the random noise signal generator is a white noise signal generator.

37. The apparatus of claim 33, further comprising a detector positioned to detect radiation from the plurality of foci light beams at the focal region, wherein the plurality of foci light beams each have a wavelength of n.

38. The apparatus of claim 37, wherein the detector detects multiphoton fluorescence radiation at a wavelength of n/x, where x is an integer.

39. The apparatus of claim 37, wherein the detector detects single-photon fluorescence radiation at a wavelength greater than n.

40. The apparatus of claim 37, wherein the detector detects the radiation at a scan rate of at least approximately 10 scans per second.

41. The apparatus of claim 33, wherein the plurality of foci light beams are arranged in an arrayed pattern.

42. The apparatus of claim 33, wherein the light beam source is controllable to adjust the intensity of the light beam, wherein adjusting the intensity of the light beam alters an intensity distribution spacing distance between adjacent ones of the plurality of foci light beams.

43. The apparatus of claim 33, further comprising a light intensity adjuster disposed to adjust the intensity of the plurality of foci light beams at the focal region.

* * * * *